United States Patent [19]

Reiterman et al.

[11] Patent Number: 5,380,245
[45] Date of Patent: Jan. 10, 1995

[54] SUCTION DELIVERY SYSTEM

[75] Inventors: Donald R. Reiterman, Hemet; Martin J. Green, El Toro; Ed F. Nicolas, Moreno Valley; Richard J. Greff, Yorba Linda; Ronald E. Thomas, Alta Loma, all of Calif.

[73] Assignee: Stackhouse, Inc., Riverside, Calif.

[21] Appl. No.: 135,302

[22] Filed: Oct. 12, 1993

Related U.S. Application Data

[63] Continuation of Ser. No. 888,974, May 24, 1992, abandoned.

[51] Int. Cl.6 ............................................. B08B 15/04
[52] U.S. Cl. ................................. 454/63; 604/313; 604/902
[58] Field of Search .............. 454/49, 63; 604/312, 604/313, 317, 319, 329, 902

[56] References Cited

U.S. PATENT DOCUMENTS

| 876,766 | 1/1908 | Blaisdell | 604/313 X |
|---|---|---|---|
| 1,148,093 | 7/1915 | Kells | 604/313 |
| 1,755,151 | 4/1930 | Henderson | 604/313 X |
| 1,944,091 | 1/1934 | Lutz | 604/313 X |
| 3,308,825 | 3/1967 | Cruse | 604/902 X |
| 4,002,170 | 1/1977 | Hansen et al. | 604/902 X |
| 4,068,664 | 1/1978 | Sharp et al. | 604/902 X |
| 4,230,114 | 10/1980 | Feather | 604/312 |
| 4,307,720 | 12/1981 | Weber, Jr. | 604/313 X |

FOREIGN PATENT DOCUMENTS

| 3325920 | 2/1985 | Germany | 604/902 |
|---|---|---|---|
| 559074 | 5/1977 | U.S.S.R. | 454/63 |
| 197710 | 10/1977 | U.S.S.R. | 454/49 |

*Primary Examiner*—Harold Joyce
*Attorney, Agent, or Firm*—Richard L. Myers

[57] ABSTRACT

A suction delivery system for removing surgical smoke from an operative site includes a hose having the configuration of a first tube and adapted to extend generally between a suction source and the operative site. A wand coupled to the distal end of the hose has the configuration of a second tube with first portions of the wand define a major suction inlet while second portions of the wand define a lateral opening which relieves suction pressure when the major inlet is blocked by tissue. A tip section of the wand includes a vane extending at least partially across the major opening and a strut extending to support the vane outwardly of the major opening. The tip section also includes means providing a laterally visible indication of the degree of contamination of the system.

26 Claims, 3 Drawing Sheets

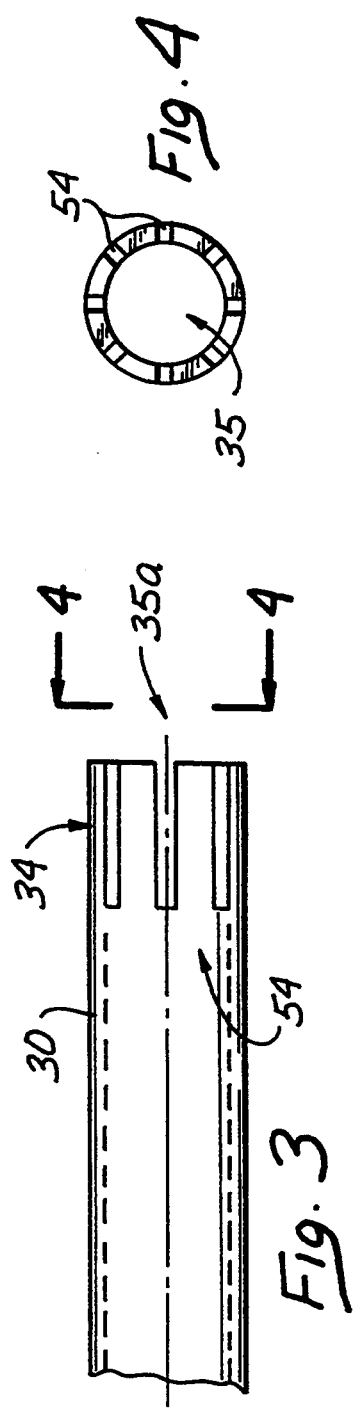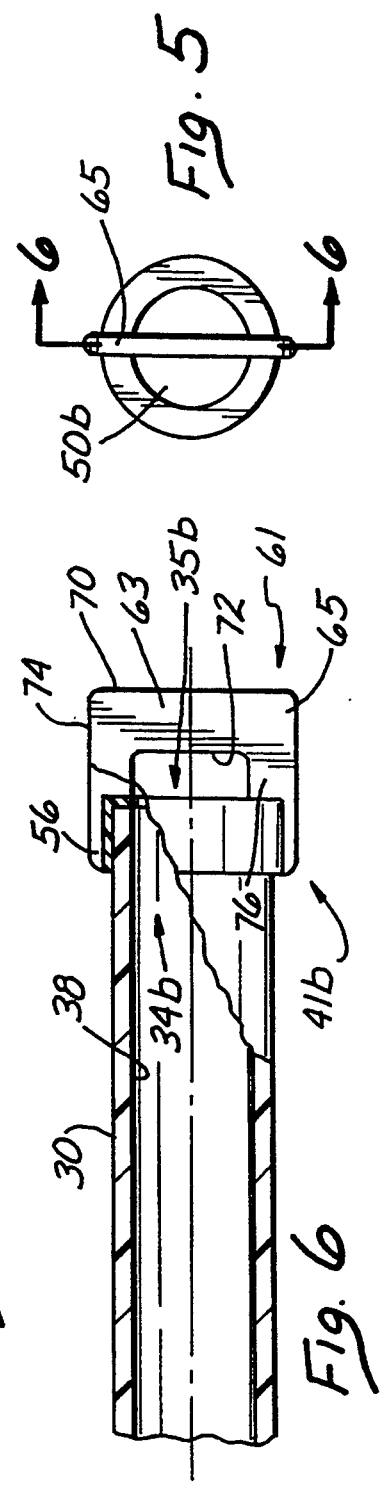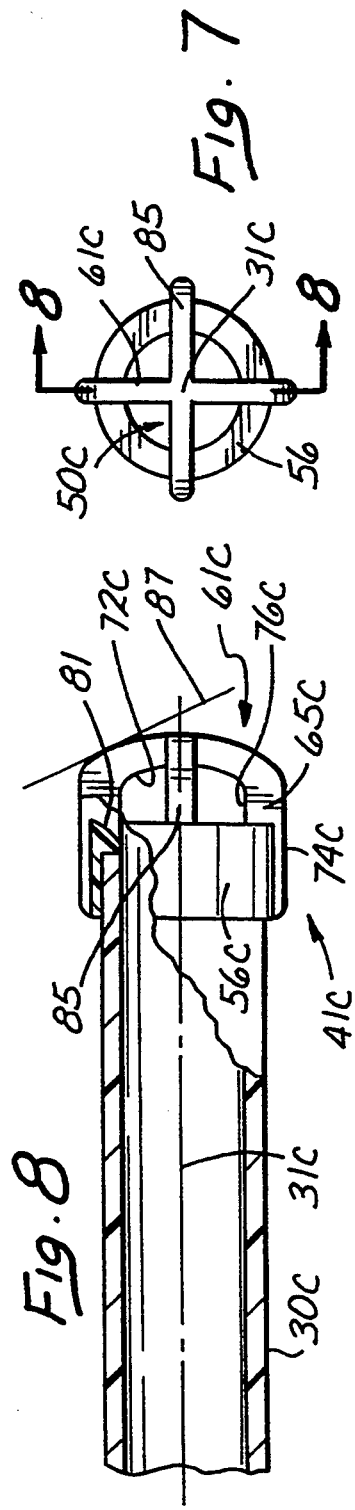

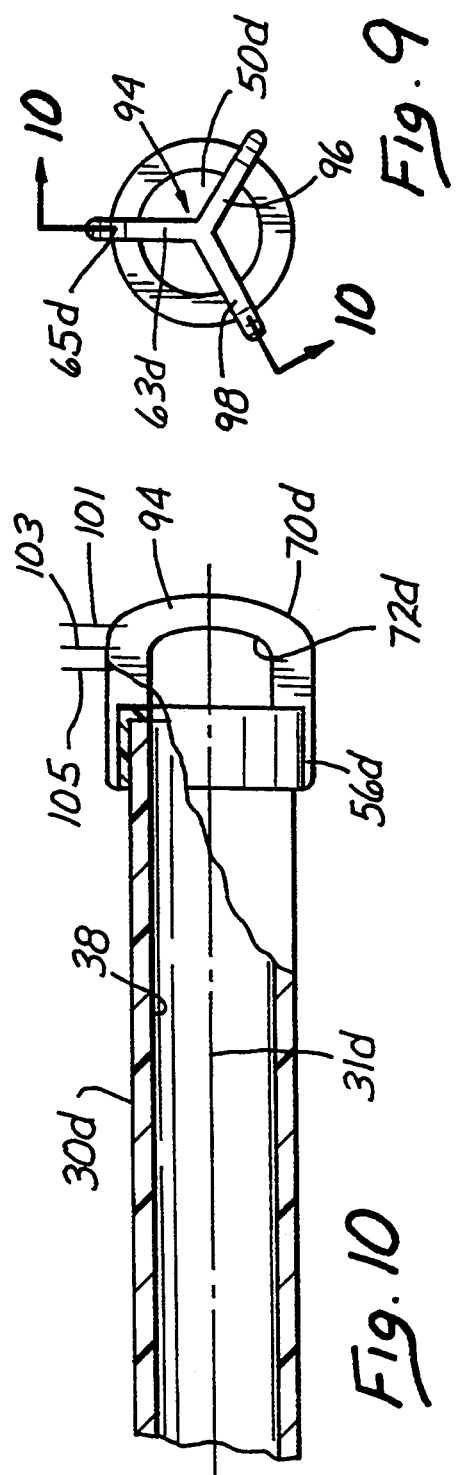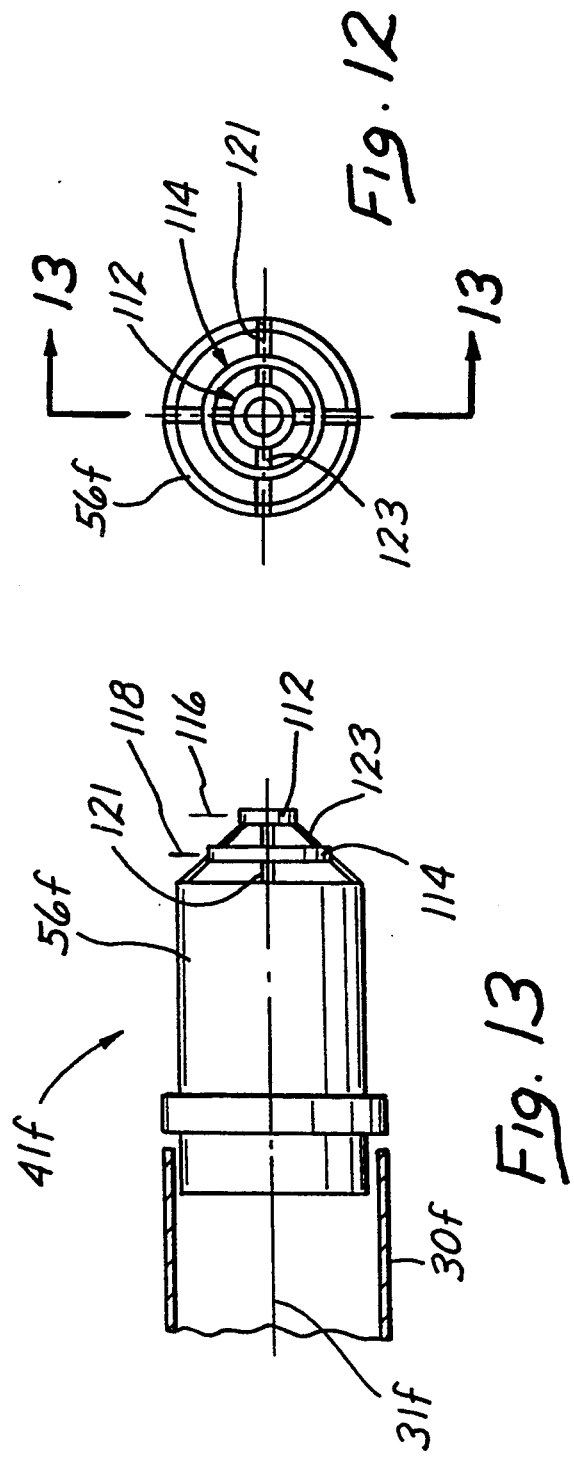

SUCTION DELIVERY SYSTEM

This is a continuation of application Ser. No. 07/888,974, filed May 24, 1992 abandoned.

BACKGROUND OF THE INVENTION

1. Field of the Invention

This invention relates generally to surgical smoke evacuators and more specifically to evacuators having delivery systems including flexible hoses and rigid wands.

2. Discussion of the Prior Art

Medical smoke evacuators of the past have included flexible hoses which extend from a source of suction/filtration/purification to a surgical site. A rigid wand has been friction fit onto the end of the flexible hose to facilitate manipulation of the hose at the surgical site. At the distal end of the wand, a major opening has been provided to permit surgical smoke and other debris to be drawn into the evacuation system. This major opening has typically been provided in a radial plane so that axial movement of the wand has sometimes blocked the opening with soft tissue.

This undesirable consequence can be better understood with an appreciation that, when in use, the smoke evacuator sucks air into the opening of the wand at a very high speed (over 100 miles per hour). It is intended that this rush of air will pick up smoke particles and other debris. However, this air can also engage squares of gauze, sponges and Other debris which are not intended to be drawn into the system.

The major opening of the wand can also attach to soft tissue which is held against the wand by atmospheric pressure against the considerable static suction (up to 100 inches of water) of the smoke evacuator. Some trauma is created in this tissue when it first engages the wand, but an even greater trauma results if an attempt is made to dislodge the wand by pulling it from the tissue. In some cases, it has been necessary to relieve the suction by stopping the smoke evacuator. This of course compromises use of the smoke evacuator and disrupts the surgical procedure.

Hoses and wands of the past have been formed from relatively expensive materials. As a consequence, the costs and sales prices associated with these devices have been substantial. Although these items are purported to be disposable, the expense of the hoses and wands have tended to encourage the users to reuse the delivery system. This is dangerous since prior use leaves the system with surgical smoke deposits on the interior surface of the hose and wand. These deposits are unsightly and odiferous, and may contain infectious agents such as virus particles, bacterial fragments and even whole bacteria. Reusing the delivery system compromises the system and puts the sterility of the surgical field at risk.

Since surgical smoke evacuators produce an air rush of such high velocity, loud and otherwise annoying sounds can be a problem. In some cases, the air rush can produce whistles which are particularly intolerable. A strong, high velocity, but quiet suction delivery system would be of significant advantage in this field of use.

SUMMARY OF THE INVENTION

In accordance with the present invention, an integral suction delivery system is provided in the form of a long flexible hose and an integral wand. This delivery system can be formed out of a relatively inexpensive material so that the disposablity of the system is assured.

The system includes a tip section which defines an axial window in a relatively radial plane and a lateral window in a generally axial plane. Tissue trauma is avoided by the lateral window which remains open even if the axial window is blocked by the tissue. Not only is the initial suction of tissue nontraumatic, but the wand can be easily removed from the tissue without stopping the smoke evacuator. The tip section of the wand is characterized by vanes and struts which are specially configured to reduce annoying sounds associated with the air rush.

In a particular aspect of the invention, a suction delivery system is adapted for use with a surgical smoke evacuator having a suction source and characteristics for removing smoke from a surgical environment. The system includes a hose adapted to extend between the source and the surgical environment with the hose having the configuration of a first tube with a proximal end coupled to the source and a distal end, the first tube being generally flexible between the proximal end and the distal end. A wand is coupled to the distal end of the hose and has the configuration of a second tube which communicates with the first tube. The wand has a proximal end attached to or integral with the hose and a distal end generally open to the surgical environment. First portions of the wand define at least one axial opening providing a major suction inlet to the hose. This axial opening has a tendency to be blocked when the wand is moved axially against tissue at the surgical site. Second portions of the wand define at least one lateral opening which is not blocked by the tissue. It is this lateral opening which reduces the suction on the blocking tissue thereby facilitating removal of the blocked wand from the tissue.

These and other features and advantages of the present invention will become more apparent with a description of preferred embodiments and reference to the associated drawings.

DESCRIPTION OF THE DRAWINGS

FIG. 3 is a side view of an additional embodiment of the wand associated with the present invention;

FIG. 4 is an end view taken along lines 4—4 of FIG. 3;

FIG. 5 is an end view similar to FIG. 4 of an additional embodiment of the tip section of the present invention;

FIG. 6 is an axial cross-section view of the wand and tip section taken along lines 6—6 of FIG. 5;

FIG. 7 is an end view of a further embodiment of the tip section of the present invention;

FIG. 8 is an axial cross-section view of the wand and tip section taken along lines 8—8 of FIG. 7;

FIG. 9 is an end view of another embodiment of the tip section of the present invention;

FIG. 10 is an axial cross-section view of the wand and tip section taken along lines 10—10 of FIG. 9;

FIG. 12 is an end view of still a further embodiment of the tip section of the present invention; and FIG. 13 is an axial cross-section view taken along lines 13—13 of FIG. 12.

DESCRIPTION OF PREFERRED EMBODIMENTS

Figure 1:
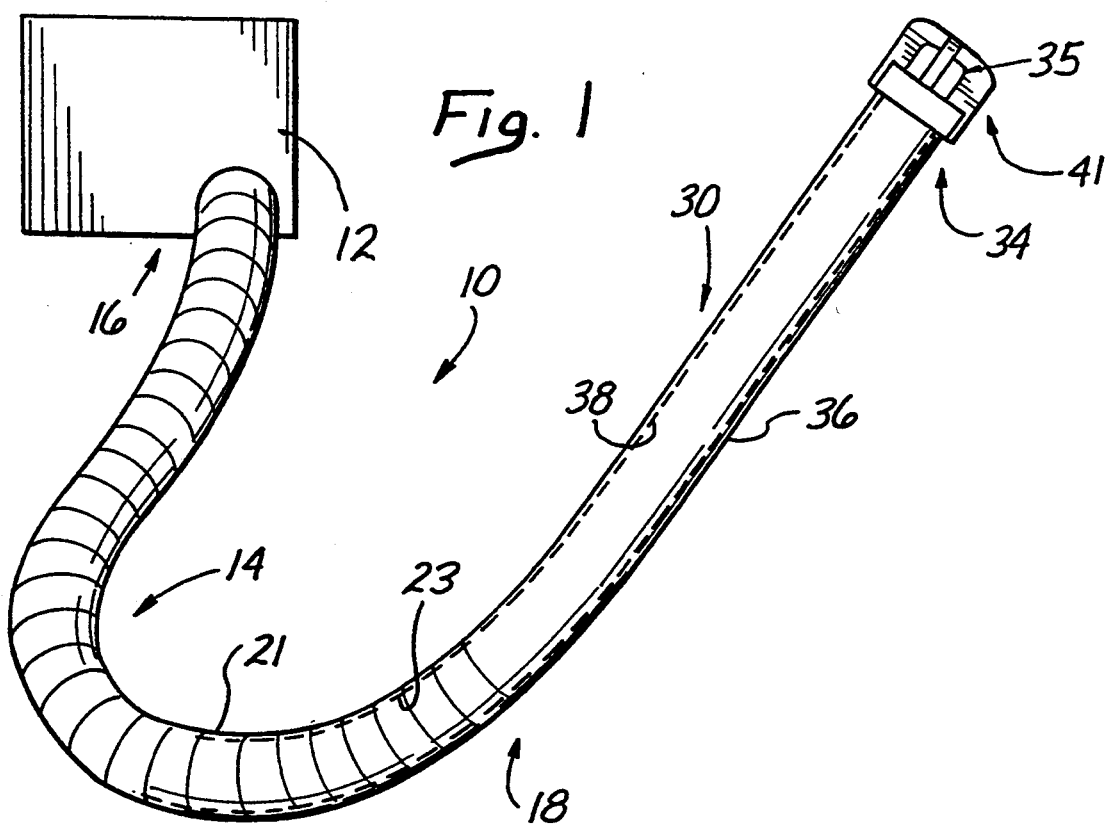
FIG. 1 is a perspective view of a suction/filtration/purification purification unit and one embodiment of a suction delivery system associated with the present invention.

A suction delivery system is illustrated in FIG. 1 and designated generally by the reference numeral 10. This system includes a suction/filtration/purification unit 12 which would typically be located in an operating room or a doctor's office. The delivery system 10 includes a long flexible hose 14 which is attached to the suction unit 12 and extends generally to an operative site (not shown) where surgical smoke is present. This smoke may result from the use of lasers or electrocautery devices for cutting, cauterizing, or otherwise coagulating tissue. The system is equally applicable for removing other fumes and noxious odors from an operative site.

The flexible hose 14 may extend approximately six feet between its proximal end 16 and its distal end 18. In a preferred embodiment, the hose 14 has a corrugated outer surface 21 which facilitates its flexibility. Although the outer surface 16 may be corrugated, it is particularly important that sharp changes in surface configuration be avoided inside the hose along the air suction path. Such undulations would tend to create turbulence and noise which would be particularly objectionable in a medical/surgical environment. For this reason, the tube forming the hose 14 is preferably provided with an inner surface 23 that is generally smooth.

The delivery system 10 also includes a wand 30, formed along an axis 31, which can be attached to the distal end 18 of the hose 14. In a preferred embodiment, the wand 30 is integral with the hose 14 in that it is formed from the same material as a single unit with the hose 14. Thus, the wand 30 includes a proximal end 32 which is either attached to or integral with the distal end 18 of the hose 14. The wand 30 also has a distal end 34 which forms a suction inlet to the delivery system 10. A tip section 41 may be attached to or molded integral with the wand 30 at the distal end 34.

The wand 30 is typically held in the hand of a user and is therefore preferably provided with a smooth outer surface 36. An inner surface 38 defines a passage through the wand which communicates with the hose 14. It is particularly desirable that the inner surface 23 of the hole 14 have the same cross-sectional configuration as the inner surface 38 of the wand 30 in order to avoid any sharp transitions in the shape of the suction channel.

Figure 2:
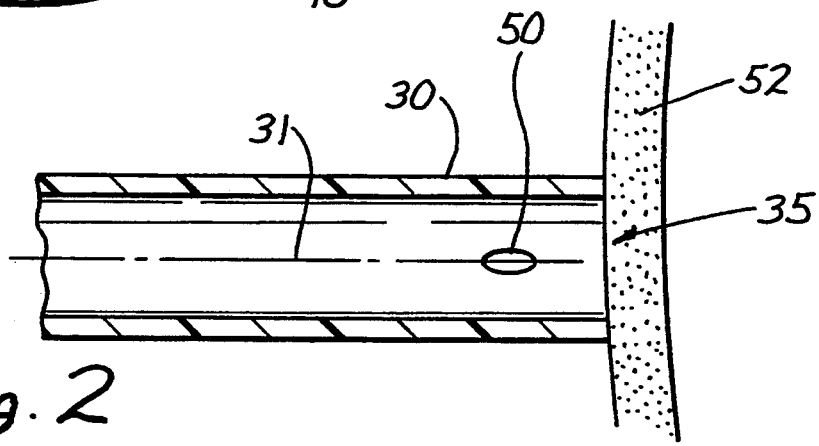
FIG. 2 is a side view of an integral wand and hose associated with the present invention with tissue locking an axial opening and a lateral opening relieving suction on the tissue.
Figure 11:
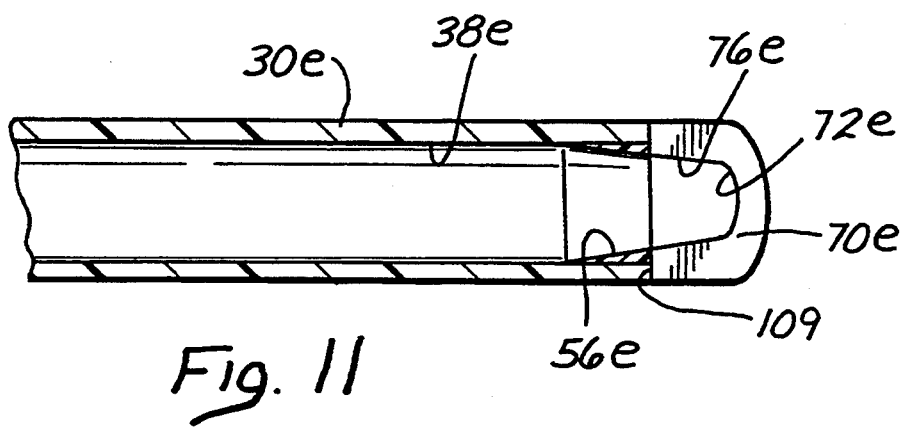
FIG. 11 is an axial cross-section view similar to FIG. 10 of an additional embodiment of the present invention.

Wands associated with the prior art have been generally open at their distal end and that distal opening has provided the only inlet to the suction channel. As previously noted, when such wands are moved axially, it is possible for them to engage and traumatize soft tissue. In order to avoid this trauma the present invention includes a lateral opening 50 which is formed near the distal end 34 of the wand 30. This opening 50 may be disposed in the tip section 41 or in the tubular portion of the wand 30 as illustrated in FIG. 2. In this figure, a wall of soft tissue 52 is shown to have been sucked up to the distal end 34 of the wand 30. Although this tissue 52 may fully block the axial opening 35, the lateral opening 50 remains unblocked and therefore relieves the suction at the opening 35. This dramatically reduces the possibility of trauma to the tissue 52.

In its broadest sense, the openings 35 and 50 are related in that they are disposed generally in different planes. For example, the axial opening 35 can be defined in a radial plane generally perpendicular to the axis 31. This opening 35 provides the major inlet for the suction delivery system 10.

In such an embodiment, the lateral opening 50 is preferably formed in a plane which forms a sharp angle with the plane of the opening 35. In the illustrated embodiment, portions of the sidewall of the tubular wand 30 define the lateral hole 50 so that the plane of the hole 50 is generally perpendicular to the plane of the opening 35. As the planes associated with the hole 50 and the opening 35 approach a perpendicular relationship, it becomes increasingly difficult for a single wall of tissue 52 to block both of the openings 35, 50. As long as one of these openings remains open, the possibility of trauma-to the soft tissue is greatly reduced.

In further embodiments of the invention similar elements of structure will be designated by the same reference numeral followed by a lower case letter. Thus in FIG. 3 the lateral opening is designated 50a and the axial opening is designated 35a. In this particular embodiment, the lateral opening 50a is formed by a plurality of windows or fenestrations 54 which extend into the axial opening 35a. These fenestrations 54 extend axially of the wand 30a and are open at the distal end 34 as best illustrated in FIG. 4. It will be noted that if the opening 35a is blocked by tissue, the fenestrations 54 will tend to remain open and thereby avoid trauma to the tissue. As best illustrated in FIG. 4, the fenestrations 54 are formed in radial planes and are equally spaced around the circumference of the wand 30a.

A preferred embodiment of the wand 30b and tip section 41b is illustrated in FIGS. 5 and 6. In this embodiment, the tip section 41b includes a skirt 56 which is dimensioned to provide a friction fit with the distal end 34b of the wand 30b. At least one vane 61 extends distally of the skirt 56 across the opening 35b of the wand 30b. The vane 61 includes a cross member 63 which is supported distally in spaced relationship with the wand 30b by a pair of struts 65. The vane 61 is typically formed in a single plane which is parallel to the axis 31b. This plane of the vane 61 actually includes the axis 31b in the case of the embodiment illustrated in FIGS. 5.

In FIG. 6, the cross member 63 is illustrated to include an outer surface 70 and an inner surface 72. Similarly the struts 65 include an outer surface 74 and an inner surface 76. In the tip section 41b of this embodiment, cross member 63 defines the radial plane associated with the axial opening 35. If the wand 30b and tip section 41b are moved axially into contact with a wall the of tissue 52, this axial opening 35b may be blocked. However, the lateral window 50b defined by the struts 65 would remain open thereby reducing trauma to the tissue 52 in the manner previously discussed.

In the interest of noise abatement, it is preferred if the inner surface 76 of the strut 65 extends with a smooth transition into the inner surface 38 associated with the wand 30. This will help avoid turbulence in the air flow, thereby reducing noise. If the vane 61 is disposed in an axial plane, the distance separating the inner surfaces 76 associated with the respective struts 65 should be equal to the inside diameter of the wand 30.

In the embodiment of FIG. 6, a sharp corner exists between the inner surface 72 of the cross member 63 and the inner surface 76 of the strut 65. It has been found that further noise can be abated by rounding this corner, for example as illustrated in the embodiment illustrated in FIGS. 7 and 8. In this case, the inner surface 72c associated with the cross member 63c gradually transitions into the surface 76c associated with the strut 65c. This embodiment also differs from that of FIG. 6 in the provision of a generally conical surface which funnels from the outside diameter of the skirt 56c into the inside diameter of the surface 38c. Thus, a surface 81 extends radially inwardly with progressive proximal positions along the axis 31.

The embodiment of FIG. 8 also illustrates that it may be desirable to include more than one vane 61c. In this case, an additional vane 85 is provided with the same characteristics associated with the vane 61c. These two vanes, 61c and 85 are equally angularly spaced across the opening 35c as best illustrated in FIG. 7.

With further reference to FIG. 8, it will be noted that the outer surface 70c of the cross member 63c can be curved so that the window 35c is angled slightly from a radial plane. In this case, the window 35c is defined generally in the plane shown a dotted line 87. As in previous embodiments, the lateral window 50c is still defined by the struts 65c in a plane generally parallel to the axis 31c. This plane which is designated by the reference numeral 90 in FIG. 7, still has a significant angle with the plane 87.

A further embodiment of the invention is illustrated in FIGS. 9 and 10 which includes three partial vanes 94, 96 and 98. In this embodiment, the partial vanes 94-98 do not extend in a single plane across the opening 35. Rather, each of the vanes 94-98 has a cross member which extends from the axis 31d radially outwardly to its supporting strut 65d. Even in this embodiment, the cross members associated with the struts 94-98 define the opening 35d while the struts 65d associated with the vanes 94-98 define the lateral opening 50d.

In the further interest of noise abatement, both the surfaces 70d and 72d associated with the vanes 94-98 have a curved configuration. While this may be the configuration of a circle in a preferred embodiment, these surfaces 70d and 72d are illustrated with elliptical configurations. In either case, the surfaces 70d and 72d extend decreasingly, radially, outwardly with progressive distal positions along the axis 31d. Thus with progressive proximal positions along the axis 31d, as illustrated by planes 101, 103 and 105, both the surface 70d and the surface 72d extend decreasingly, radially, outwardly. The ellipse forming the surface 72d has a maximum length equal to the inside diameter of the wand 30d so that the surface 72d extends smoothly onto the surface 38d. Similarly, the ellipse associated with the outer surface, 70d has a maximum length equal to the diameter of the outer surface of the skirt 56d so that the surface 70d transitions smoothly onto the outer surface of the skirt 56d. In this embodiment, the width of the respective ellipse forming the surfaces 70d and 72d are chosen such that the vanes 94-98 have a reduced thickness in proximity to the axis 31d.

In still a further embodiment of the invention, the tip section 41e is provided with an inner skirt 56e which forms a friction fit with the inner surface 38e of the wand 30e. In this case, the tip section 41e extends inwardly of the wand 30e and the inner surfaces 72e, 76e and 38e form a continuous surface free of undulations. A shoulder 109 is formed between the inner skirt 56e and the vane 61e so that the outer surface 70e of the vane 61e transitions smoothly onto the outer surface associated with the wand 30e.

Still a further embodiment of the invention is illustrated in FIGS. 12 and 13 where the wand is designated by the reference numeral 30f. In this case, the tip section 41f includes vanes 112 and 114 which are cylindrical and concentric with the axis 31f. The cylinders forming the vanes 112 and 114 have a narrow axial dimension and are disposed primarily in radial planes 116 and 118, respectively. The vane 114 is supported by struts 121 which extend from the skirt 56f, and the vane 112 is supported by struts 123 which extend from the vane 114. Both the struts 121 and 123 extend radially inwardly with progressive positions in the distal direction. In the illustrated embodiment, the angle between the strut 121 and the axis 31f is the same as the angle between the struts 123 and the axis 31f.

In all of these embodiments including vanes in the tip section 41, the wand 30 benefits from a further advantage associated with the invention. These vanes not only extend across the axial opening 35, but actually divide this large opening into a plurality of smaller openings. As a consequence, large pieces of tissue and other objects, such as sponges and specimens, which would otherwise fit into the axial opening 35 are restricted from the suction channel.

A further advantage of the invention is associated with the wand structure and its ability to provide a visual indication as to the degree of contamination of the system 10. Each of the vanes 61, 94-98, and the associated strut 65, has a lateral surface 125 which is disposed in the path of the surgical smoke but which can be viewed laterally of the surface 125. For example, the surface 125 in each of the embodiments of FIGS. 5, 7, and 9 faces laterally of the wand and is unobstructed for viewing from a lateral position. Since this surface 125 is disposed in the path of the surgical smoke, particles from the smoke tend to collect on the surface 125. If the surface 125 is provided with a color which contrasts with the normally dark color of the smoke particles, a build up of the particles over time provides a visual indication in the form of increasing contrast with the surface 125. Since this contrast is immediately viewable from a position lateral to the surface 125, a surgeon can readily determine the degree of contamination of the system 10.

In a further embodiment, the surface 125 may be provided with a coating 127, such as a flat white enamel, which readily attracts the smoke particles and enhances the degree of contrast which provides the visual indication of contamination. As the particles build up on the coating 127, the contrast increases providing a variable and gradual indication as to the amount of smoke which has passed through the wand 30. In either embodiment, this indication will be provided as a function of not only smoke concentration but also time. Thus, the degree of contamination will be indicated whether the deliver system 10 is used to filter a large quantity of smoke for a short period of time or filter a small quantity of smoke for a long period of time.

Although the invention has been described with respect to specific embodiments of the concept, it will be appreciated that the invention can be otherwise structured and configured. Different numbers of vanes, such as the vane 61, can be formed to extend either fully or partially across the opening 35. The size and number of lateral openings 50 may also vary depending on the number of vanes. While it may be desirable to increase the number of vanes in order to reduce the possibility of trauma to soft tissue, these vanes increase the possibility of noise due to the high velocity of air. However, as noted, this noise can be abated by avoiding sharp transitions between adjacent surfaces and otherwise providing for a smooth flow of air into the wand 30.

Given these variations, all within the scope of the present invention, one is cautioned not to rely entirely on the embodiments described and illustrated, but rather to determine the scope of invention with reference to the following claims.

We claim:

1. A surgical smoke evacuation system, comprising:
   a surgical smoke evacuator for removing smoke from a surgical environment;
   a hose adapted to extend between the evacuator and the surgical environment, the hose including a first tube with a proximal end coupled to the evacuator and a distal end, the first tube being generally flexible between the proximal end of the first tube and the distal end of the first tube;
   a wand integral with the distal end of the hose for delivering the suction of the evacuator at a predetermined flow rate appropriate for removing the smoke from the surgical environment, the wand including a second tube with a proximal end attached to the hose and a generally open distal end having a cross sectional area sized for admitting the smoke from the surgical environment at the predetermined flow rate, the second tube communicating with the first tube and being generally rigid between the proximal end of the second tube and the distal end of the second tube;
   first means included in the wand for defining at least one axial opening providing a major suction inlet into the hose, the axial opening having a tendency to become blocked when the wand is moved axially against tissue;
   second means included in the wand for defining at least one lateral opening at a location displaced from the first means a distance sufficient to inhibit blockage of the lateral opening by the tissue during axial movement of the wand; whereby
   the lateral opening reduces the suction of the tissue blocking the at least one axial opening thereby facilitating removal of the blocked wand from the tissue.

2. The surgical smoke evacuation system recited in claim 1 wherein the wand further comprises:
   a tip fixed to the distal end of the second tube and including the first portions of the wand which define the axial opening and the second portions of the wand which define the lateral opening.

3. The surgical smoke evacuation system recited in claim 2 wherein the second tube has an axis, the axial opening is disposed generally in a radial plane, and the lateral opening is defined generally in a plane parallel to the axis of the second tube.

4. The surgical smoke evacuation system recited in claim 3 wherein the first portions which define the axial opening are integral with the second portions which define the lateral opening, and the first opening is common with the second opening.

5. The surgical smoke evacuation system recited in claim 4 wherein the axial opening extend into the lateral opening forming a single hole in the tip portion of the wand.

6. A surgical smoke evacuator for removing surgical smoke from an operative site, including:
   a source of suction;
   a hose adapted to provide a fluid conduit for the surgical smoke from the operative site to the source of suction, the hose having the configuration of a first tube with a proximal end coupled to the source and a distal end;
   a wand coupled to the distal end of the first tube and having the configuration of a second tube with a proximal end attached to the first tube and a distal end defining a major opening extending across an axis of the second tube, the second tube being generally rigid between the proximal end of the second tube and the distal end of the second tube; and
   a tip section disposed at the distal end of the second tube and including portions of the tip section defining the major opening of the second tube, portions of the tip section defining at least one vane extending at least partially across the major opening and at least one strut extending relative to the major opening to support the vane.

7. The surgical smoke evacuator recited in claim 6 wherein the vane has a length not less than the radius of the major opening.

8. The surgical smoke evacuator recited in claim 7 wherein:
   the major opening has a perimeter and the tip section includes at least three vanes equally angularly spaced around the major opening and each extending from the axis of the major opening outwardly to the perimeter of the major opening; and
   three struts each supporting an associated one of the vanes at the perimeter of the major opening.

9. The surgical smoke evacuator recited in claim 6 further comprising a coating on the tip section providing a visual indication of the degree of contamination of the tip section.

10. The surgical smoke evacuator recited in claim 6 wherein the wand is integral with the hose.

11. The surgical smoke evacuator recited in claim 6 wherein:
    the vane has an outer surface with the configuration of at least a portion of a first curve having a first length and a first width, and an inner surface having the configuration of at least a portion of a second curve having a second length and second width;
    the first length being greater than the diameter than the second tube at the major opening; and
    the second length being less than the diameter of the major opening.

12. The surgical smoke evacuator recited in claim 11 wherein the vane has an axial thickness which becomes increasingly thicker with progressive positions radially of the axis.

13. The surgical smoke evacuator recited in claim 6 wherein the strut extends generally axially of the major opening.

14. The surgical smoke evacuator recited in claim 6 wherein the strut extends radially inwardly with progressive positions distally of the major opening.

15. The surgical smoke evacuator recited in claim 14 wherein the vane has the configuration of a cylinder and is disposed in a radial plane.

16. A surgical smoke evacuator adapted for use with a source of suction to remove surgical smoke from an operative site, including:

a hose extending between the source of suction and the operative site, the hose having the configuration of a first tube with a proximal end adapted to be coupled to the source of suction and a distal end adapted to be disposed at the surgical site;

a wand coupled to the distal end of the first tube and having the configuration of a second tube with a proximal end attached to the first tube and a distal end generally opened to the operative site, the second tube communicating with the first tube and being generally rigid between the proximal end of the second tube and the distal end of the second tube;

a tip disposed at the distal end of the wand;

first portions of the tip defining a major opening facing generally in an axial direction;

second portions of the tip defining a secondary opening facing generally in a radial direction; and the first portions including a vane extending at least partially across the major opening.

17. The surgical smoke evacuator recited in claim 16 wherein the second portions include at least one strut extending at least partially across the secondary opening and supporting the vane.

18. The surgical smoke evacuator recited in claim 16 wherein the vane in axial cross-section has an outer surface with the shape of a portion of a first ellipse having a first length and a first width, and an inner surface with the shape of a portion of a second ellipse having a second length and second width, the first length being greater than the second length and the first width being greater than the second width.

19. The surgical smoke evacuator recited in claim 16 wherein the vane is defined by a pair of edges each extending in a generally radial direction.

20. The surgical smoke evacuator recited in claim 19 wherein the edges are generally parallel.

21. The surgical smoke evacuator recited in claim 17 wherein the strut is defined by a pair of edges each extending in a generally axial direction.

22. The surgical smoke evacuator recited in claim 16 wherein the tip has a skirt which is sized and configured for frictional engagement with the distal end of the wand.

23. The surgical smoke evacuator recited in claim 22 wherein the skirt is disposed exteriorly of the wand.

24. The surgical smoke evacuator recited in claim 16 wherein:

the tube of the wand has an axis;

the vane is a first vane configured generally in the shape of a first ring having a coaxial relationship with the tube; and the tip further comprises a second vane configured generally in the shape of a second ring having a coaxial relationship with the tube and the first ring.

25. A surgical smoke evacuator for use in removing surgical smoke from an operative site, including:

a source of suction;

a hose extending between the source of suction and the operative site, the hose having the configuration of a first tube with a proximal end coupled to the source of suction and a distal end disposed at the operative site;

a wand coupled to the distal end of the first tube and having the configuration of a second tube with a proximal end attached to the first tube and a distal end generally open to the operative site, the second tube communicating with the first tube and being generally rigid between the proximal end of the second tube and the distal end of the second tube;

a substrate forming a tip of the wand and being disposed in the path of the surgical smoke, the substrate having properties attractive to the particles of smoke and a color contrasting with the color of the smoke particles;

first portions of the tip defining a major opening disposed generally in a radial plane;

second portions of the tip defining a lateral opening disposed generally in a plane other than the radial plane;

the first portions of the tip including a vane extending at least partially across the major opening; and means disposed at the distal end of the wand for providing a visual indication of the degree of contamination of the wand by the surgical smoke.

26. The surgical smoke evacuator recited in claim 25 wherein the vane in axial cross-section has an outer surface with the shape of a portion of a first ellipse having a first length and a first width, and an inner surface with the shape of a portion of a second ellipse having a second length and second width, the first length being greater than the second length and the first width being greater than the second width.

* * * * *